(12) United States Patent
Miller et al.

(10) Patent No.: US 8,188,069 B2
(45) Date of Patent: May 29, 2012

(54) AZEPINE DERIVATIVES AS GAMMA-SECRETASE INHIBITORS

(75) Inventors: Melinda Joy Hope Miller, Morgantown, IN (US); Warren Jaye Porter, Indianapolis, IN (US); Jon Kevin Reel, Carmel, IN (US); Almudena Rubio-Esteban, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 371 days.

(21) Appl. No.: 12/669,048

(22) PCT Filed: Aug. 4, 2008

(86) PCT No.: PCT/US2008/072049
§ 371 (c)(1),
(2), (4) Date: Jan. 14, 2010

(87) PCT Pub. No.: WO2009/023453
PCT Pub. Date: Feb. 19, 2009

(65) Prior Publication Data
US 2010/0197660 A1   Aug. 5, 2010

Related U.S. Application Data

(60) Provisional application No. 60/955,720, filed on Aug. 14, 2007.

(51) Int. Cl.
*A61K 31/55* (2006.01)
*C07D 223/12* (2006.01)
*A61P 25/28* (2006.01)

(52) U.S. Cl. ............................. 514/212.03; 540/527
(58) Field of Classification Search ............. 514/212.03; 540/527
See application file for complete search history.

(56) References Cited

U.S. PATENT DOCUMENTS
7,468,365 B2   12/2008   Audia et al.

FOREIGN PATENT DOCUMENTS
| WO | 98/28268 A | 7/1998 |
| WO | 02/47671 A2 | 6/2002 |
| WO | 2004/031154 A | 4/2004 |
| WO | 2004/080983 A | 9/2004 |

*Primary Examiner* — Sreeni Padmanabhan
*Assistant Examiner* — Sahar Javanmard
(74) *Attorney, Agent, or Firm* — Nelson L. Lentz; Elizabeth A. Dingess-Hammond

(57) ABSTRACT

Compounds of formula (I), pharmaceutical compositions comprising them, and methods for their use are described.

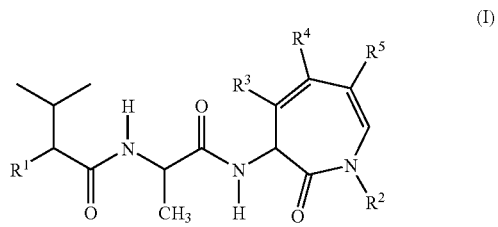

8 Claims, No Drawings

AZEPINE DERIVATIVES AS GAMMA-SECRETASE INHIBITORS

This application is a United States national phase entry, pursuant to 35 U.S.C. 371, of PCT/US2008/072049, filed Aug. 4, 2008, which claims the benefit of U.S. Provisional patent application Ser. No. 60/995,720, filed Aug. 14, 2007.

Alzheimer's disease, characterized by cognitive and behavioral deterioration in its latter stages, has emerged as a significant social and financial concern. Neurofibrillary tangles and neuritic plaques are generally found in the brain regions associated with memory and cognition of those afflicted with Alzheimer's disease. These plaques are also found in the brains of individuals with Down's syndrome, Hereditary Cerebral Hemorrhage of the Dutch-Type, and other neurodegenerative disorders. The neuritic plaques are comprised primarily of amyloid β (Aβ) peptide, a neurotoxic and highly aggregatory peptide segment of amyloid precursor protein (APP). Aβ peptide is formed by the proteolytic cleavage of APP by β-secretase (BACE) followed by at least one subsequent C-terminal cleavage by γ-secretase. As such, inhibition of γ-secretase is an attractive target for the treatment or prevention of Alzheimer's disease as well as other diseases characterized by amyloid plaques. Inhibitors of γ-secretase taught to be useful for the treatment of Alzheimer's disease and other disorders are known in the art (WO 98/28268 and WO 04/080983). The present invention provides additional inhibitors of γ-secretase. Certain compounds of the present invention exhibit a favorable therapeutic index.

This invention provides compounds of Formula I:

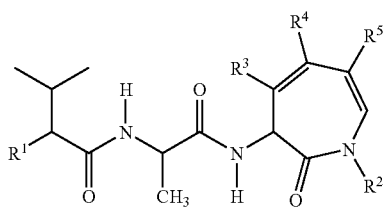

where:
R$^1$ is hydroxy or fluoro;
R$^2$ is C$_1$-C$_4$ alkyl;
R$^3$ is hydrogen or phenyl;
R$^4$ is hydrogen, phenyl, or C$_1$-C$_4$ alkyl;
R$^5$ is hydrogen or phenyl; provided that one of R$^3$, R$^4$, and R$^5$ is other than hydrogen and the other two are hydrogen.

In another embodiment, this invention provides a pharmaceutical composition comprising a compound of Formula I and a pharmaceutically acceptable diluent. The invention also provides for the use of a compound of Formula as a pharmaceutical.

In one of its method aspects, this invention is directed to a method of lowering amyloid β peptide in a patient comprising administering to said patient an effective amount of a compound of Formula I. The invention also provides the use of a compound of Formula I for the preparation of a medicament for lowering amyloid β protein.

In a particular method embodiment, the present invention provides a method for treating Alzheimer's disease comprising administering to a patient in need thereof an effective amount of a compound of Formula I. The invention also provides the use of a compound of Formula I for the preparation of a medicament for treating Alzheimer's disease.

The present invention also provides a method for preventing or inhibiting the progression of Alzheimer's disease comprising administering to a patient in need thereof an effective amount of a compound of Formula I. The invention also provides the use of a compound of Formula I for the preparation of a medicament for preventing or inhibiting the progression of Alzheimer's disease.

The general chemical terms used in the formulae above have their usual meanings. For example, the term "C$_1$-C$_4$ alkyl" includes methyl, ethyl, propyl, isopropyl, butyl, isobutyl, sec-butyl, and tert-butyl.

The term "nitrogen protecting group" is taken to mean a moiety that is stable to projected reaction conditions and yet may be selectively removed by reagents and reaction conditions compatible with the regenerated amine Such groups are well known by the skilled artisan and are described in the literature. (See, for example: Greene and Wuts, *Protective Groups in Organic Synthesis*, Third Edition, Chapter 7, John Wiley and Sons Inc., (1999)). Nitrogen protecting groups contemplated include suitable carbamates, such as tert-butoxycarbonyl.

The skilled artisan will understand that all of the compounds of Formula I have at least 3 chiral centers marked with "*" in the following structure:

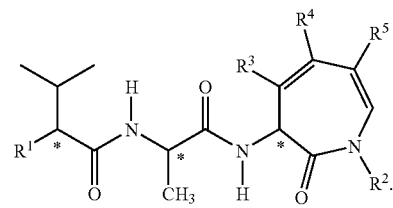

Although this invention contemplates all individual diastereomers, as well as mixtures of diastereomers of said compounds including racemates, the diastereomer preferred for compounds of Formula I is as illustrated in Figure (i):

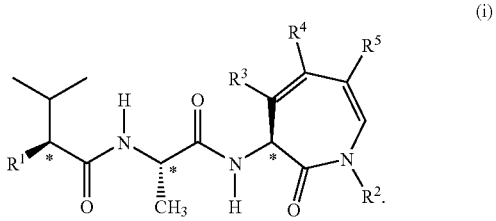

The compounds of Formula I are useful inhibitors of γ-secretase, but certain classes of compounds are preferred. The following paragraphs describe such preferred classes:

a) R$^1$ is hydroxy;
b) R$^2$ is methyl;
c) R$^4$ is hydrogen or phenyl
d) R$^4$ is phenyl;
e) A compound of Formula I where R$^2$ is methyl and R$^4$ is phenyl;
f) A compound of Formula I where R$^1$ is hydroxy, R$^2$ is methyl, and R$^4$ is phenyl; and g) The compound of formula (ii):

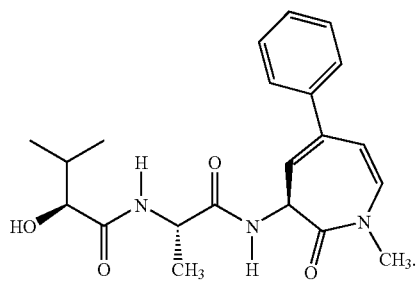

The compounds of Formula I are inhibitors of γ-secretase. Thus, this invention also provides a method of inhibiting γ-secretase in a mammal that comprises administering to a mammal in need of said treatment a γ-secretase-inhibiting amount of a compound of Formula I. It is preferred that the mammal to be treated by the administration of the compounds of Formula I is human.

As inhibitors of γ-secretase, the compounds of the present invention are useful for suppressing the production of A-β peptide, and therefore for the treatment of disorders resulting from excessive Aβ peptide levels. The compounds of Formula I are therefore believed to be useful in treating or preventing Alzheimer's disease, mild cognitive impairment, Down's Syndrome, Hereditary Cerebral Hemorrhage with Amyloidosis of the Dutch-Type, cerebral amyloid angiopathy, other degenerative dementias such as: dementias of mixed vascular and degenerative origin, dementia associated with Parkinson's disease, dementia associated with progressive supranuclear palsy, dementia associated cortical basal degeneration, and diffuse Lewy body type of Alzheimer's disease.

The compounds of the present invention may be prepared by a variety of procedures, some of which are illustrated in the Schemes below. It will be recognized by one of skill in the art that the individual steps in the following schemes may be varied to provide the compounds of Formula I. The particular order of steps required to produce the compounds of Formula I is dependent upon the particular compound being synthesized, the starting compound, and the relative lability of the substituted moieties. Furthermore, individual isomers, enantiomers, or diastereomers may be separated at any convenient point in the synthesis of compounds of Formula I.

The compounds of Formula I may be prepared as described in the following scheme where variables $R^2$, $R^3$, $R^4$, and $R^5$ are as previously defined and variable Pg is a nitrogen protecting group.

Scheme I

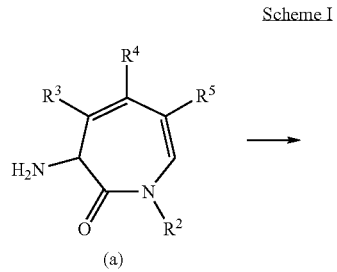

-continued

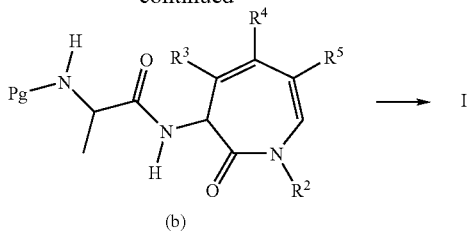

The amine (a) is reacted under standard amide forming conditions well known to the skilled artisan to provide amide (b). A suitably nitrogen-protected alanine, for example N-(tert-butoxycarbonyl)-alanine or an equivalent thereof, such as the sodium or potassium carboxylate salt is reacted with a peptide coupling agent such as dicyclohexylcarbodiimide (DCC), 1-(3-dimethylaminopropyl)-3-ethylcarbodiimide hydrochloride (EDC), or n-propylphosphonic anhydride, and an appropriate amine such as N-methylmorpholine, diisopropylethylamine or triethylamine, in a suitable solvent such as dichloromethane, dimethylformamide (DMF) or tetrahydrofuran (THF) to provide the amide (b). If necessary or required, an additive such as 4-(dimethylamino)pyridine and/or 1-hydroxybenzotriazole or equivalents thereof may be added to the reaction mixture to facilitate the reaction. Alternatively, other carboxylic acid equivalents, including acylating agents, such as an appropriate acylimidazole or an appropriate acid halide may be reacted directly with the amine (a) to provide the desired amide (b). The amide (b) is then deprotected under conditions well known to the skilled artisan. (For example, see: Greene and Wuts, *Protective Groups in Organic Synthesis*, Third Edition, Chapters 2 and 7, John Wiley and Sons Inc., (1999)) This resulting amine is then reacted with either 2-hydroxyisovaleric acid or 2-fluoroisovaleric acid under the standard amide coupling conditions previously described to provide the compounds of Formula I.

The requisite amines (a) may be prepared as described in the following scheme where variables $R^2$, $R^3$, $R^4$, and $R^5$ are as previously defined, X is —$NR_aR_b$ or —$OR_a$, and variables $R_a$ and $R_b$ are independently $C_1$-$C_4$ alkyl.

Scheme II

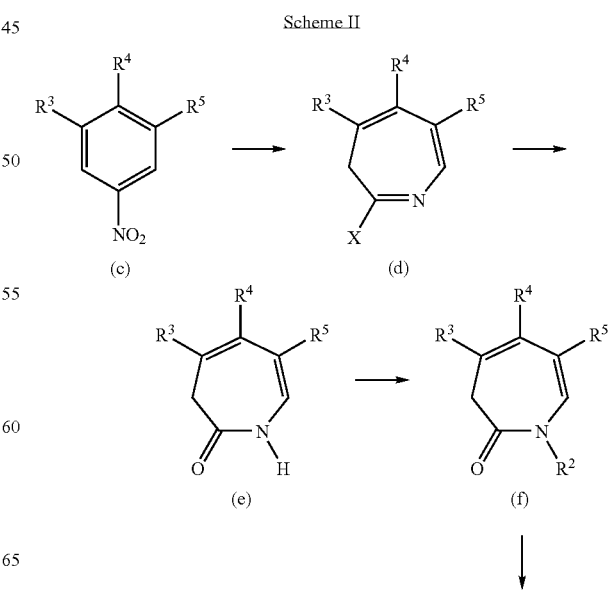

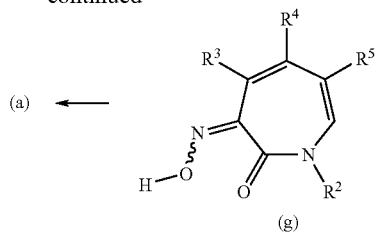

An appropriately substituted nitrobenzene (c) is reacted with either an appropriate amine and phosphorus triamide at elevated temperature in a sealed tube to provide intermediate (d) where X is —$NR_aR_b$, or an appropriate $C_1$-$C_4$ alcohol and trialkylphosphine at elevated temperature in a sealed tube to provide intermediate (d) where X is —$OR_a$. Intermediate (d) is then reacted with water to provide lactam (e). This lactam is then N-alkylated under standard conditions, for example, by reaction with an alkyl halide in the presence of a suitable base, such as potassium tert-butoxide or cesium carbonate, to prepare the N-alkylated lactam (f). The requisite amine moiety may be introduced by reaction of lactam (f) with a suitable base, such as potassium tert-butoxide, followed by reaction with isoamyl nitrite to provide the oxime (g). This oxime is then reduced under standard conditions, for example, by reaction with zinc dust in acetic acid, to provide the desired amine (a).

Preparation 1

Diethyl-(5-phenyl-3H-azepin-2-yl)-amine

A mixture of 4-nitro-biphenyl (26.35 g, 132.3 mmol), diethylamine (137.0 mL, 1.32 mol), and hexaethylphosphorus triamide (72.6 mL, 265.0 mmol) is divided between two pressure tubes. The tubes are sealed and the contents heated to 120-125° C. for 16 hours. After cooling to room temperature, the contents of the pressure tubes are combined and concentrated in vacuo. The residue is washed with water (2×100 mL). The aqueous insoluble material is diluted with dichloromethane, washed with water (100 mL), and extracted with 1N HCl (2×150 mL). The aqueous acid layer is washed with dichloromethane (3×200 mL). The aqueous acid layer is made alkaline with NaOH pellets (pH 12) and extracted with dichloromethane. The organic layer is washed with saturated aqueous sodium chloride, dried over $MgSO_4$, and concentrated in vacuo to give 6.89 g (22%) of the title intermediate as a dark brown oily solid contaminated with a small amount of hexaethylphosphoramide. The dichloromethane washings from the acid layer are dried over $MgSO_4$ and concentrated in vacuo to give 80 g of a dark brown liquid consisting of approximately 66% hexaethylphosphoramide and 34% of the title intermediate as the HCl salt. This material is diluted with dichloromethane (100 mL) and extracted with 1N HCl (2×100 mL). The combined aqueous layers are made alkaline (pH 13) with NaOH pellets and extracted with dichloromethane (2×300 mL). The combined organic layers are washed with saturated aqueous sodium chloride, dried over $MgSO_4$, and concentrated in vacuo to give 18.81 g of the title intermediate as dark brown crystals which are contaminated with approximately 30% hexaethylphosphoramide. The title compound is carried into the next reaction without further purification.

MS: (m/z)=241.2 (M+1).

The following compounds are prepared essentially by the method of Preparation 1.

| Prep. | Compound | MS (m/z) |
| --- | --- | --- |
| 2 | Diethyl-(5-isopropyl-3H-azepin-2-yl)-amine | 207.3 M + 1) |
| 3 | Mixture of diethyl-(4-phenyl-3H-azepin-2-yl)-amine and diethyl-(6-phenyl-3H-azepin-2-yl)-amine. | — |

Preparation 4

5-Phenyl-1,3-dihydro-azepin-2-one

The crude diethyl-(5-phenyl-3H-azepin-2-yl)-amine (12.47 g) is added to water (10.0 mL) and 2-methoxy-ethanol (40.0 mL) and the resulting mixture heated to reflux and stirred 4½ days. The volatiles are removed in vacuo and the residue diluted with dichloromethane and washed with 0.1N HCl (2×200 mL) and saturated aqueous $NaHCO_3$ (2×200 mL). The organic layer is dried over $Na_2SO_4$ and concentrated in vacuo to give the crude title compound as a dark brown solid (9.63 g). This material is carried into the next reaction without further purification.

MS: (m/z)=186.1 (M+1).

The following compounds are prepared essentially by the method of Preparation 4.

| Prep. | Compound | MS (m/z) |
| --- | --- | --- |
| 5 | 5-Isopropyl-1,3-dihydro-azepin-2-one | 152.1 (M + 1) |
| 6 | Mixture of 4-phenyl-1,3-dihydro-azepin-2-one and 6-phenyl-1,3-dihydro-azepin-2-one | — |

Preparation 7

2-Butoxy-5-phenyl-3H-azepine

A 22 Liter reaction flask is equipped with a heating mantle, overhead stirring apparatus, condenser, addition funnel, thermometer probe, and nitrogen inlet/outlet. The flask is purged thoroughly with nitrogen and maintained under nitrogen throughout the reaction. The flask is charged with 4-nitrobiphenyl (1700 g, 8.53 moles) and 1-butanol (3793 g, 51.2 moles). The resulting mixture is heated to reflux to form a clear solution. Tributylphosphine (3500 g, 17.3 moles) is charged to the addition funnel and added dropwise to the hot 4-nitrobiphenyl solution. The temperature is gradually increased as needed to maintain reflux. The reaction is monitored by gas chromatography analysis for completion. The reaction is cooled and water is added (500 mL). The reaction is concentrated to an oil, followed by the addition of petroleum ether (8.0 L). The resulting mixture is cooled to −40° C. and filtered to remove undesired tributylphosphine oxide. The filtrate is concentrated again and petroleum ether (8.0 L) is added. The mixture is cooled and filtered. The resulting filtrate is concentrated to an oil and purified by silica gel chromatography to give the title compound (908 g, 44%).

MS: (m/z)=242.1 (M+1).

Preparation 8

5-Phenyl-1,3-dihydro-azepin-2-one

The 2-butoxy-5-phenyl-3H-azepine (908 g, 3.42 moles) is dissolved in 2B-3 ethanol (8172 mL) and de-ionized water (2724 mL). The solution is charged to an autoclave and heated to 150° C. for 20 hours. The solution is cooled to room temperature and concentrated under reduced pressure. Residual water is removed by azeotropic distillation from toluene (2×2 L). The residual solids are dissolved in toluene (1.7 L) and heated between 95 to 100° C. The solution is cooled to <90° C. and heptane (about 4.8 mL/g) is added. The solution is allowed to cool to room temperature, and then cooled to 0 to 5° C. using an ice bath. The solids are filtered, washed with heptane, and dried to give the title compound (559 g, 88%) as a light brown solid.

MS(EI): (m/z)=185.1

Preparation 9

1-Methyl-5-phenyl-1,3-dihydro-azepin-2-one

The 5-phenyl-1,3-dihydro-azepin-2-one (168.5 g, 911.3 mmol) is combined with tetrahydrofuran (1300 mL) and the solution cooled to about −30° C. Potassium tertiary-butoxide (107.4 g, 956.9 mmol) is added in one portion. Exotherm is observed warming the reaction contents to −12° C. Upon subsiding of the exotherm, the contents are allowed to re-cool to −25° C. and iodomethane (113.5 mL, 1.823 moL) is added providing a slight exotherm. The reaction contents are allowed to warm to room temperature and stirred. After 10 hours the reaction mixture is diluted with methyl tertiary-butyl ether (1300 mL) and extracted with saturated ammonium chloride solution (2×250 mL), water, and saturated aqueous sodium chloride solution. The combined aqueous layers are back extracted with methyl tertiary-butyl ether (200 mL). The methyl tertiary-butyl ether extracts are combined, dried over MgSO$_4$ and filtered. The solution is concentrated via rotary evaporation to provide the title compound (185 g, 100%) as a brown powdery residue. The material is used directly, without purification, in the next step.

The following compounds are prepared essentially by the method of Preparation 9.

| Prep. | Compound | MS (m/z) |
|---|---|---|
| 10 | 5-Isopropyl-1-methyl-1,3-dihydro-azepin-2-one | 166.2 (M + 1) |
| 11 | 1-Methyl-4-phenyl-1,3-dihydro-azepin-2-one | Exact mass: Calculated: 200.1075, Found: 200.1058 |
| 12 | 1-Methyl-6-phenyl-1,3-dihydro-azepin-2-one | Exact mass: Calculated: 200.1075, Found: 200.1077 |

Preparation 13

1-Methyl-5-phenyl-1H-azepine-2,3-dione 3-oxime

The 1-methyl-5-phenyl-1,3-dihydro-azepin-2-one (183 g, 918.4 mmol) is combined with tetrahydrofuran (1500 mL) and the solution cooled to −25° C. to −30° C. Isoamyl nitrite (148.1 mL, 1.102 mol) is added followed by potassium tertiary-butoxide (108.2 g, 964.4 mmol) providing an exotherm to about −5° C. The solution is re-cooled to −10° C., then allowed to slowly warm to room temperature. The reaction contents are allowed to stir overnight. The reaction contents are diluted with 3N aqueous HCl (300 mL) providing a pH of about 2. It is then diluted with methyl tertiary-butyl ether (4 L) and washed the contents with 0.5-1.0 N HCl (2×600 mL) and saturated aqueous sodium chloride. The dark organic layer is dried over MgSO$_4$, filtered, and concentrated to provide a residue wet with tetrahydrofuran. The residue is diluted with cyclohexane (300 mL) and concentrated to provide about 275 g of a crude residue that is slurried in methyl tertiary-butyl ether (450 mL) and cyclohexane (1000 mL). Heat the slurry to about 40° C., cool to room temperature, filter, and rinse with cyclohexane. Vacuum dry at 40° C. to provide the title compound (169 g, 81%) as a brown powder.

The following compounds are prepared essentially by the method of Preparation 13.

| Prep. | Chemical Name | MS (m/z) |
|---|---|---|
| 14 | 5-Isopropyl-1-methyl-1H-azepine-2,3-dione-3-oxime | 195.1 (M + 1) |
| 15 | 1-Methyl-6-phenyl-1H-azepine-2,3-dione 3-oxime | Exact mass: Calculated: 229.0977, Found: 229.0975 |
| 16 | 1-Methyl-4-phenyl-1H-azepine-2,3-dione 3-oxime | Exact mass: Calculated: 229.0977, Found: 229.0980 |

Preparation 17

3-amino-1-methyl-5-phenyl-1,3-dihydro-azepin-2-one

1-Methyl-5-phenyl-1H-azepine-2,3-dione 3-oxime (25 g, 109 mmol) is combined with acetic acid (80 mL), methanol (80 mL) and water (40 mL) and the slurry is cooled to about 5° C. Zinc dust (29.81 g, 436 mmol) is added in portions. The reaction contents are allowed to cool back to room temperature. After 2 hours the reaction contents are filtered over a Celite® pad and rinsed with methanol. The filtrate is concentrated via rotary evaporation until a majority of the methanol is removed. The oily purple solution is then diluted with dichloromethane (200 mL) causing some immediate precipitation. The thick slurry is filtered to remove the zinc acetate as a white powder. The resulting purple filtrate is further diluted with dichloromethane (200 mL) and extracted with ammonium hydroxide solution (2×100 mL). The organic extracts are dried over MgSO$_4$, filtered, and concentrated to provide 21.5 g (92%) of a purple oil. Upon dilution with warm ethyl acetate (200 mL) a fine precipitate is observed and removed by filtration. The remaining ethyl acetate solution is treated with gaseous hydrogen chloride (about 5 g, 137 mmol) to provide a thick slurry initially which thins upon full addition of the hydrogen chloride. After stirring the slurry at room temperature for 2 hours, the contents are filtered and vacuum dried at 45° C. to afford the HCl salt of the title intermediate (22.9 g, 94%) as a brown powder. The 22.9 g of HCl salt is treated with 150 mL of 1N sodium hydroxide and dichloromethane. The layers are allowed to separate and the dichloromethane layer is further washed with saturated sodium bicarbonate solution. The dichloromethane solution is then dried over magnesium sulfate, filtered and concentrated to provide 19.6 g of the title compound as a red-brown oil.

The following compounds are prepared essentially by the method of Preparation 17.

| Prep. | Compound | MS (m/z) |
|---|---|---|
| 18 | 3-Amino-5-isopropyl-1-methyl-1,3-dihydro-azepin-2-one | 181.1 (M + 1) |
| 19 | 3-Amino-1-methyl-4-phenyl-1,3-dihydro-azepin-2-one | Exact mass (sodium salt): Calculated: 237.1004, Found: 237.1001 |
| 20 | 3-Amino-1-methyl-6-phenyl-1,3-dihydro-azepin-2-one | Exact mass: Calculated: 214.1106, Found: 214.1105 |

Preparation 21

(S)-[1-(1-methyl-2-oxo-5-phenyl-2,3-dihydro-1H-azepin-3-ylcarbamoyl)-ethyl]-carbamic acid tert-butyl ester 3-Amino-1-methyl-5-phenyl-1,3-dihydro-azepin-2-one (330 g, 1.54 mol) is combined with dichloromethane (3 L), N-(tert-butoxycarbonyl)-L-alanine (291.4 g, 1.54 mol), and hydroxybenzotriazole hydrate (259.5 g, 1.617 mol). The solution is cooled to about 10° C. To this solution is added diisopropylethylamine (335.4 mL, 1.925 mol) followed by 1-(3-dimethylaminopropyl)-3-ethylcarbodiimide hydrochloride (310.1 g, 1.617 mol) and the contents are allowed to gradually warm to room temperature. After 3.5 hours, the reaction contents are poured into water (1000 mL) and the layers are allowed to separate. The organic layer is further washed with water (1000 mL), 0.1 N HCl (1000 mL), saturated $NaHCO_3$ solution (1000 mL) and finally saturated aqueous sodium chloride solution. The dichloromethane layer is dried over $Na_2SO_4$, filtered, and concentrated via rotary evaporation to provide the title compound (about 574 g, 97%) as a tan foam. The material is of sufficient purity to use directly in the next step.

The following compounds are prepared essentially by the method of Preparation 21.

| Prep. | Compound | MS (m/z) |
|---|---|---|
| 22 | [(S)-1-(5-Isopropyl-1-methyl-2-oxo-2,3-dihydro-1H-azepin-3-ylcarbamoyl)-ethyl]-carbamic acid tert-butyl ester | 352.1 (M + 1) |
| 23 | [(S)-1-(1-Methyl-2-oxo-4-phenyl-2,3-dihydro-1H-azepin-3-ylcarbamoyl)-ethyl]-carbamic acid tert-butyl ester | Exact mass (sodium salt): Calculated: 408.1899, Found: 408.1896 |
| 24 | [(S)-1-(1-Methyl-2-oxo-6-phenyl-2,3-dihydro-1H-azepin-3-ylcarbamoyl)-ethyl]-carbamic acid tert-butyl ester | Exact mass: Calculated: 386.2080, Found: 386.2073 |

Preparation 25

(S)-2-amino-N-(1-methyl-2-oxo-5-phenyl-2,3-dihydro-1H-azepin-3-yl)-propionamide

To a cooled solution of trifluoroacetic acid (800 mL) at −5° C. is added a solution of the (S)-[1-(1-methyl-2-oxo-5-phenyl-2,3-dihydro-1H-azepin-3-ylcarbamoyl)-ethyl]-carbamic acid tert-butyl ester (564 g, 1.46 mol) in dichloromethane (2 L) via an addition funnel The reaction contents are stirred at 0° C. for 2 hours at which point a reaction aliquot shows only a trace amount of the starting material remaining. The reaction contents are concentrated via rotary evaporation, re-diluted with dichloromethane and re-concentrated to provide a syrup. The syrupy oil is diluted with dichloromethane (2-3 L) and added to 10% sodium carbonate solution (2 L). Additional 10% sodium carbonate solution (2 L) is required to render a basic pH of the aqueous layer. The layers are separated and the aqueous layer back-extracted with dichloromethane (600 mL). The combined organic layers are then extracted with saturated sodium bicarbonate (1000 mL), dried over sodium sulfate, filtered and concentrated via rotary evaporation to provide the title intermediate (about 435 g) as an oily foam, approximately 406 g (97%) of which is the title compound.

The following compounds are prepared essentially by the method of Preparation 25.

| Prep. | Compound | MS (m/z) |
|---|---|---|
| 26 | (S)-2-Amino-N-(5-isopropyl-1-methyl-2-oxo-2,3-dihydro-1H-azepin-3-yl)-propionamide | 252.1 (M + 1) |
| 27 | (S)-2-Amino-N-(1-methyl-2-oxo-6-phenyl-2,3-dihydro-1H-azepin-3-yl)-propionamide hydrochloride | Exact mass: Calculated: 286.1556, Found: 286.1558 |
| 28 | (S)-2-Amino-N-(1-methyl-2-oxo-4-phenyl-2,3-dihydro-1H-azepin-3-yl)-propionamide hydrochloride | Exact mass: Calculated: 286.1556, Found: 286.1548 |

Preparation 29

(S)-2-Fluoro-3-methyl-butyric acid

Charge a 3-gallon Nalgene® container with triethylamine tri-hydrofluoride (4.06 L, 25.1 mol), (S)-2-amino-3-methyl-butanoic acid (147.9 g, 1.26 moL) and sodium nitrite (113 g, 1.64 mol). Stir at room temperature 12-15 hrs. Pour into cold water (5 L) and diethyl ether (7 L) in a Nalgene® container. Stir and then allow the layers to separate. Wash the organic phase with water (3 L). Extract the combined aqueous layers with diethyl ether (3 L). Wash the combined organic layers with water (3 L) and then with saturated aqueous sodium bicarbonate. Adjust the pH of the saturated aqueous sodium bicarbonate layer a pH<4 with 1N sulfuric acid. Extract with diethyl ether (2×2 L), dry over magnesium sulfate, filter and concentrate under reduced pressure by rotary evaporation ensuring the bath temperature does not exceed 30° C. to provide 60 g of the title compound as an oil with about 85-90% purity and an enantiomeric excess of about 60%.

Preparation 30

Enantiomeric Excess Enrichment of (S)-2-fluoro-3-methyl-butyric acid

The 2-fluoro-3-methylbutyric acid (~235.5 g, 1.96 mol), is taken up in ethyl acetate (2.9 L) and R-(+)-α-methylbenzylamine (237.5 g, 1.96 mol) is added dropwise via an addition funnel. A temperature rise to 40° C. is observed. Upon allowing the solution to cool, a slurry results and is stirred at room temperature for 45 minutes. The slurry is then filtered and the filter cake rinsed with ethyl acetate (300 mL). The wet cake is suspended in ethyl acetate (4.5 L) and heated to reflux. Additional ethyl acetate (450 mL) is added to provide a solution, and then the solution is allowed to stand at room temperature overnight. The resulting slurry is filtered and the filter cake rinsed with ethyl acetate (200 mL). The filter cake is vacuum dried at 40° C. to afford 262.3 g of the (R)-+-α-methylbenzylamine salt of (S)-2-fluoro-3-methylbutyric acid as a powder. The enantiomeric excess of this salt is found to be >94% by chiral capillary electrophoresis analysis for the desired (S) isomer.

The (R)-+-α-methylbenzylamine salt of (S)-2-fluoro-3-methylbutyric acid (252 g, 1.044 mol) is added to 1 N hydrochloric acid (1472 mL) and extracted into diethyl ether (2×2.5 L). The organic layers are combined and washed with 1 N hydrochloric acid (600 mL), dried over magnesium sulfate, filtered, and concentrated under reduced pressure by rotary evaporation ensuring the bath temperature does not exceed 30° C. to provide 122 g of (S)-2-fluoro-3-methylbutyric acid in 97.2% yield as a clear oil. The enantiomeric excess of the acid is found to be 96% by chiral capillary electrophoresis analysis.

EXAMPLE 1

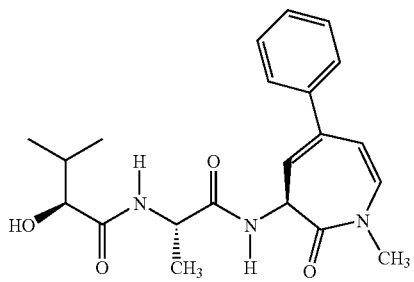

(S)-2-hydroxy-3-methyl-N-[(S)-1-((S)-1-methyl-2-oxo-5-phenyl-2,3-dihydro-1H-azepin-3-ylcarbamoyl)-ethyl]-butyramide The (S)-2-amino-N-(1-methyl-2-oxo-5-phenyl-2,3-dihydro-1H-azepin-3-yl)-propionamide (406 g, 1.423 mol) is combined with dichloromethane (3 L) and the solution cooled to 0-2° C. To this solution is added (S)-2-hydroxy-3-methyl-butyric acid (168.1 g, 1.423 mol), hydroxybenzotriazole hydrate (239.7 g, 1.565 mol) and diisopropylethylamine (310 mL, 1.779 mol) which provides a slight exotherm. The contents are cooled back to about 4° C. and 1-(3-dimethylaminopropyl)-3-ethylcarbodiimide hydrochloride (286.5 g, 1.494 mol) is added. The reaction contents are allowed to gradually warm to room temperature. High-performance liquid chromatography analysis at 4.5 hours (temperature at 14° C.) indicates about 5% unreacted starting amine present. After stirring an additional 1-1.5 hour, the reaction contents are quenched into water (1000 mL) and the layers are separated. The dichloromethane layer is further extracted with water (1000 mL), 0.1 N HCl (1000 mL), saturated sodium bicarbonate (1000 mL) and finally saturated aqueous sodium chloride. The dichloromethane layer is then dried over magnesium sulfate, filtered and concentrated via rotary evaporation to provide the crude diastereomeric mixture (505 g) of the coupled product as tan foam. The isomers are separated by chiral chromatography employing a Chiralpak® AD column eluting with 100% methanol. Upon removal of the elution solvent from the isomer fractions, approximately 210 g of the first eluting isomer is recovered as a tan foam and for the desired isomer 2, approximately 220 g (44%) is recovered, also as a tan powder. The second eluting isomer is the desired (S,S,S)-diastereomer. Approximately 140 g of the title compound is taken up in acetone (1000 mL) and water (95 mL). The solution is heated on the rotary evaporator until no suspended particles are observed. The solution is transferred to a flask, equipped with overhead stirring, and water (2750 mL) is gradually added over 15 minutes. The resulting slurry is allowed to cool to room temperature, then filtered and the cake is rinsed with 20% acetone/water solution (650 mL). After vacuum drying at 40° C. overnight, approximately 102 g of the title example is recovered.

MS (m/z): 386.2 (M+1).

The following compounds are prepared essentially by the method of EXAMPLE 1.

| EXAMPLE | Compound | MS (m/z) |
|---|---|---|
| 2 | (S)-2-Fluoro-3-methyl-N-[(S)-1-(1-methyl-2-oxo-5-phenyl-2,3-dihydro-1H-azepin-3-ylcarbamoyl)-ethyl]-butyramide | Exact mass: Calculated: 388.2036 Found: 388.2021. |
| 3 | (S)-2-Hydroxy-N-[(S)-1-(5-isopropyl-1-methyl-2-oxo-2,3-dihydro-1H-azepin-3-ylcarbamoyl)-ethyl]-3-methyl-butyramide | 352.3 (M + 1) |
| 4 | (S)-2-Hydroxy-3-methyl-N-[(S)-1-(1-methyl-2-oxo-4-phenyl-2,3-dihydro-1H-azepin-3-ylcarbamoyl)-ethyl]-butyramide | Exact mass: Calculated: 386.2080; Found: 386.2075. |
| 5 | (S)-2-Hydroxy-3-methyl-N-[(S)-1-(1-methyl-2-oxo-6-phenyl-2,3-dihydro-1H-azepin-3-ylcarbamoyl)-ethyl]-butyramide | Exact mass: Calculated: 386.2080; Found: 386.2078. |
| 6 | (S)-2-Fluoro-3-methyl-N-[(S)-1-(1-methyl-2-oxo-6-phenyl-2,3-dihydro-1H-azepin-3-ylcarbamoyl)-ethyl]-butyramide | Exact mass: Calculated: 388.2037; Found: 388.2031. |

EXAMPLE 7

Determination of Absolute Configuration of (S)-2-hydroxy-3-methyl-N-[(S)-1-((S)-1-methyl-2-oxo-5-phenyl-2,3-dihydro-1H-azepin-3-ylcarbamoyl)-ethyl]-butyramide Crystals were grown by vapor diffusion of n-pentane into a solution of (S)-2-Hydroxy-3-methyl-N-[(S)-1-((S)-1-methyl-2-oxo-5-phenyl-2,3-dihydro-1H-azepin-3-ylcarbamoyl)-ethyl]-butyramide (EXAMPLE 1, second eluting fraction) dissolved in dichloromethane. A single crystal of (S)-2-hydroxy-3-methyl-N-[(S)-1-((S)-1-methyl-2-oxo-5-phenyl- 2,3-dihydro-1H-azepin-3-ylcarbamoyl)-ethyl]-butyramide is mounted on a thin glass fiber and immersed in a stream of nitrogen at −173° C. Data are collected using a MoKα radiation source (λ=0.71073 Å) and a P4 diffractometer equipped with a SMART 1000CCD area detector (Bruker-AXS. Madison, Wis., USA). Cell refinement and data reduction are performed using the SAINT program (Sheldrick, G M. *SHELXS*86, *Acta Cryst*. A46, 467-473 (1990)). The unit cell is indexed, having orthorhombic parameters of a=8.010(5)Å, b=20.345(15)Å, c=25.513(19)Å. The cell volume of crystal structure is 4157(5). Å 3 and has a density of 1.232 g/cm3, having two molecules in its unit cell. The structure is solved by direct methods (Sheldrick, G. M., *SHELXS*93, Institute fur anorg chemie, Göttingen, Germany). All atomic parameters are independently refined. The space group choice, that is $P2_12_12_1$, is confirmed by successful convergence of the full-matrix least-squares refinement on F2 with a final goodness of fit off 1.297. The final residual factor, R1, is =0.1905 and the largest difference peak and hole after the final refinement cycle are 0.988 and −0.754 (e.A−3), respectively.

Two of the stereogenic centers are set by the purchase of commercial material with defined stereochemistry (N-(tert-butoxycarbonyl)-L-alanine in Preparation 21 and (S)-2-hydroxy-3-methyl-butyric acid in Example 1). There is no evidence of significant stereochemical erosion at either of these two stereogenic centers during its synthesis, therefore the relative stereochemistry of the crystal structure is used to define the third stereogenic center as (S) in the second eluting diastereomer of Example 1.

EXAMPLE A

In Vitro Inhibition of β-Amyloid Production

The ability of compounds to inhibit β-amyloid production is evaluated in a cell line possessing the Swedish mutation. This screening assay employed cells (HEK293=human kidney cell line) which were stably transfected with the gene for amyloid precursor protein 751 (APP751) containing the double mutation $Lys_{651}Met_{652}$ to $Asn_{651}Leu_{652}$ (APP751 numbering) in the manner described in International Patent Application Publication No. 94/10569. This mutation is commonly called the Swedish mutation and the cells, designated as "293 751 SWE", were plated in Corning 96-well plates at $2-4\times10^4$ cells per well in Dulbecco's minimal essential media (Sigma, St. Louis, Mo.) plus 10% fetal bovine serum. Cell number is important in order to achieve β-amyloid ELISA results within the linear range of the assay (~0.03 to 1.0 ng per mL).

Following overnight incubation at 37° C. in an incubator equilibrated with 5% carbon dioxide, media are removed and replaced with a stock solution of test compound (200 μL per well) for a two hour incubation period. Drug stocks are prepared in 100% dimethyl sulfoxide such that at the final drug concentration used in the treatment, the concentration of dimethyl sulfoxide does not exceed 0.5% and usually equals 0.1%.

At the end of the incubation period, 100 μL from each well, of conditioned media or appropriate dilutions thereof are transferred into an ELISA plate pre-coated with antibody 266 [P. Seubert, *Nature* (1992) 359:325-327] against amino acids 13-28 of β-amyloid peptide as described in International Patent Application Publication No. 94/10569 and stored at 4° C. overnight. An ELISA assay employing labeled antibody 3D6 [P. Seubert, *Nature* (1992) 359:325-327] against amino acids 1-5 of β-amyloid peptide is run the next day to measure the amount of β-amyloid peptide produced. The results of the β-amyloid peptide ELISA are fit to a standard curve and expressed as ng/mL β-amyloid peptide and the concentration of test compounds producing 50% inhibition ($IC_{50}$) of β-amyloid peptide production are estimated using a four parameter logistic model within Graph Pad Prism (San Diego, Calif.).

The effects of the compounds on cellular protein synthesis are measured by assessing the incorporation of [$^{35}$S]methionine into total cellular protein in compound-treated 293 751 SWE cells. $2-4\times10^4$ 293 751 SWE cells/well in poly-D-lysine-coated Cytostar-T® microtiter plates (Amersham, Piscataway, N.J.) are treated for 2 h with various concentrations of test compounds prepared in methionine-free DMEM containing 1% FBS, 20 mM HEPES, and 1 μCi [$^{35}$S]methionine (43.5 TBq/mmol; New England Nuclear, Boston, Mass.). Following incubation with test compounds, the incorporation of [$^{35}$S]-methionine into total cellular protein is determined in methanol-fixed, PBS-washed cells using a Wallac Micobeta scintillation counter (PerkinElmer, Boston, Mass.).

At least one diastereomer of the exemplified compounds exhibited an $IC_{50} \leq 1$ μM when tested essentially as described above. The following compounds were tested essentially as described above and were found to have the following activity:

| EXAMPLE* | $IC_{50}$ (μM) |
| --- | --- |
| 1 (diasteromer 1) | 0.390 ± 0.014 (n = 3) |
| 1 (diasteromer 2) | 0.005 ± 0.0007 (n = 3) |
| 2 (diastereomer 1) | 3.33 ± 0.43 (n = 3) |
| 2 (diastereomer 2) | 0.008 ± 0.0008 (n = 3) |
| 3 (diastereomer 1) | 10.7 ± 1.8 (n = 3) |
| 3 (diastereomer 2) | 0.036 ± 0.001 (n = 3) |

*As used herein, the phrase "diastereomer 1" refers to the first eluting diastereomer and "diastereomer 2" refers to the second eluting diastereomer of the compound referred to by specific EXAMPLE number.

EXAMPLE B

In Vivo Suppression of β-Amyloid Release and/or Synthesis

This example illustrates how the compounds of this invention could be tested for in vivo suppression of β-amyloid release and/or synthesis. For these experiments, 3 to 4 month old PDAPP mice are used [Games et al., (1995) *Nature* 373: 523-527]. Depending upon which compound is being tested, the compound is usually formulated at between 1 and 10 mg/mL. Because of the low solubility factors of the compounds, they may be formulated with various vehicles, such as corn oil; 10% ethanol in corn oil; 2-hydroxypropyl-β-cyclodextrin (Research Biochemicals International, Natick, Mass.); and carboxy-methyl-cellulose (Sigma Chemical Co., St. Louis, Mo.).

For acute efficacy studies, PDAPP mice are dosed orally by gavage and 3 hours later the animals are euthanized via $CO_2$ narcosis. For sub-chronic studies, PDAPP mice are dosed once-a-day or twice-a-day for 7 days, and sacrificed 3 hours after the last dose. Blood is taken by cardiac puncture using a 1 cc 25G ⅝" tuberculin syringe/needle coated with solution of 0.5 M EDTA, pH 8.0. The blood is placed in a Becton-Dickinson vacutainer tube containing EDTA and spun down for 15 minutes at 1500×g at 5° C. The brains of the mice are then removed and the cortex and hippocampus are dissected out, placed in labeled eppendorf tubes and rapidly frozen on dry ice.

Brain Assay

To prepare hippocampal and cortical tissue for enzyme-linked immunosorbent assays (ELISAs) each brain region is homogenized in 10 volumes of ice cold guanidine buffer (5.0 M guanidine-HCl, 50 mM Tris-HCl, pH 8.0) using a Polytron. The homogenates are gently rocked on a rotating platform for three to four hours at room temperature and stored at −20° C. prior to quantitation of β-amyloid.

The brain homogenates are diluted 1:10 with ice-cold casein buffer [0.25% casein, phosphate buffered saline (PBS), 0.05% sodium azide, 20 μg/ml aprotinin, 5 mM EDTA, pH 8.0, 10 μg/ml leupeptin], thereby reducing the final concentration of guanidine to 0.5 M, before centrifugation at 16,000×g for 20 minutes at 4° C. Samples are further diluted, if necessary, to achieve an optimal range for the ELISA measurements by the addition of casein buffer with 0.5 M guanidine hydrochloride added. The β-amyloid standards (1-40 or 1-42 amino acids) are prepared such that the final composition equaled 0.5 M guanidine in the presence of 0.1% bovine serum albumin (BSA).

The Total β-amyloid 1-x sandwich ELISA, quantitating essentially all species of β-amyloid (including β-amyloid 1-40 and β-amyloid 1-42), employs two monoclonal antibodies (mAb) to β-amyloid. The capture antibody, 266 [P. Seubert, *Nature* (1992) 359:325-327], is specific to amino acids 13-28 of β-amyloid. The antibody 3D6 [Johnson-Wood et al., *PNAS USA* (1997) 94:1550-1555], which is specific to amino acids 1-5 of β-amyloid, is biotinylated and served as the reporter antibody in the assay. The 3D6 biotinylation procedure employs the manufacturer's (Pierce, Rockford, Ill.) protocol for NHS-biotin labeling of immunoglobulins except that 100 mM sodium bicarbonate, pH 8.5 buffer is used. The 3D6 antibody does not recognize secreted amyloid precursor protein (APP) or full-length APP but detects only β-amyloid species with an amino terminal aspartic acid. The assay has a lower limit of sensitivity of ~50 pg/ml (11 pM) and shows no cross-reactivity to the endogenous murine β-amyloid peptide at concentrations up to 1 ng/ml.

The configuration of the sandwich ELISA quantitating the level of β-amyloid (aa 1-42) employs the mAb 21F12 [Johnson-Wood et al., *PNAS USA* (1997) 94:1550-1555] (which recognizes amino acids 33-42 of β-amyloid) as the capture antibody. Biotinylated 3D6 is also the reporter antibody in this assay which has a lower limit of sensitivity of ~125 pg/ml (28 pM).

The 266 and 21F12 capture mAbs are coated at 10 μg into 96-well immunoassay plates (Costar, Cambridge, Mass.) overnight at room temperature. The plates are then aspirated and blocked with 0.25% human serum albumin in PBS buffer for at least 1 hour at room temperature, then stored desiccated at 4° C. until use. The plates are rehydrated with wash buffer (Tris-buffered saline, 0.05% Tween 20) prior to use. The samples and standards are added to the plates and incubated overnight at 4° C. The plates are washed 3 times with wash buffer between each step of the assay. The biotinylated 3D6, diluted to 0.5 μg/ml in casein incubation buffer (0.25% casein, PBS, 0.05% Tween 20, pH 7.4) is incubated in the well for 1 hour at room temperature. Avidin-HRP (Vector, Burlingame, Calif.) diluted 1:4000 in casein incubation buffer is added to the wells for 1 hour at room temperature. The colormetric substrate, Slow TMB-ELISA (Pierce, Cambridge, Mass.), is added and allowed to react for 15 minutes, after which the enzymatic reaction is stopped with addition of 2 N $H_2SO_4$. Reaction product is quantified using a Molecular Devices Vmax (Molecular Devices, Menlo Park, Calif.) measuring the difference in absorbance at 450 nm and 650 nm.

The compound of EXAMPLE 1 (second eluting diastereomer) was tested essentially as described above and was found to have the following activity:

| Hippocampal Total A-beta Reduction* | |
| --- | --- |
| DOSE (mg/kg) | % REDUCTION** |
| 0.1 | 18% (n = 1) |
| 0.3 | 31 ± 13% (n = 2) |
| 1 | 48 ± 11% (n = 3) |
| 3 | 59 ± 5% (n = 5) |
| 10 | 69% (n = 1) |

*Young (8-13 week old) heterozygous PDAPP mice; oral administration; sacrifice at 3 hours post-administration.
**MEAN ± Standard Deviation (n of 1-5 experiments, each with an n of 6-8 mice/dose)

Blood Assay

The EDTA plasma is diluted 1:1 in specimen diluent (0.2 gm/l sodium phosphate.$H_2O$ (monobasic), 2.16 gm/l sodium phosphate.$7H_2O$ (dibasic), 0.5 gm/l thimerosal, 8.5 gm/l sodium chloride, 0.5 ml Triton X-405, 6.0 g/l globulin-free bovine serum albumin; and water). The samples and standards in specimen diluent are assayed using the total β-amyloid assay (266 capture/3D6 reporter) described above for the brain assay except the specimen diluent is used instead of the casein diluents described.

The compound of EXAMPLE 1 (second eluting diastereomer) was tested essentially as described above and was found to reduce plasma A-beta by 54% (p<0.001 relative to vehicle control) at a dose of 3 mg/kg (b.i.d. for 7 days).

It is also recognized that one skilled in the art may affect Alzheimer's disease by treating a patient presently afflicted with the disease or by prophylactically treating a patient at risk to develop the disease. Thus, the terms "treatment" and "treating" are intended to refer to all processes wherein there may be a slowing, interrupting, arresting, controlling, or stopping of the progression of Alzheimer's disease, but does not necessarily indicate a total elimination of all symptoms. As such, the present methods include preventing the onset of Alzheimer's disease in a patient at risk for developing Alzheimer's disease, inhibiting the progression of Alzheimer's disease, and treatment of advanced Alzheimer's disease.

As used herein, the term "effective amount" of a compound of Formula I refers to an amount which is effective in lowering Aβ peptide levels in a patient, and specifically, in treating Alzheimer's disease.

Oral administration of the compounds of the present invention is preferred. However, oral administration is not the only route or even the only preferred route. For example, transdermal administration may be very desirable for patients who are forgetful or petulant about taking oral medicine, and the intravenous route may be preferred as a matter of convenience or to avoid potential complications related to oral administration. Compounds of Formula I may also be administered by the percutaneous, intramuscular, intranasal or intrarectal route in particular circumstances. The route of administration may be varied in any way, limited by the physical properties of the drugs, the convenience of the patient and the caregiver, and other relevant circumstances (*Remington's Pharmaceutical Sciences,* 18th Edition, Mack Publishing Co. (1990)).

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations of the present invention may be determined by methods well known to the skilled artisan.

The tablets, pills, capsules, troches, and the like may also contain one or more of the following adjuvants: binders such as povidone, hydroxypropyl cellulose, microcrystalline cellulose, or gelatin; excipients or diluents such as: starch, lactose, microcrystalline cellulose or dicalcium phosphate, disintegrating agents such as: croscarmellose, crospovidone, sodium starch glycolate, corn starch and the like; lubricants such as: magnesium stearate, stearic acid, talc or hydrogenated vegetable oil; glidants such as colloidal silicon dioxide; wetting agents such as: sodium lauryl sulfate and polysorbate 80; and sweetening agents such as: sucrose, aspartame or saccharin may be added or a flavoring agent such as: peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, as coatings. Thus, tablets or pills may be coated with sugar, hydroxypropyl methylcellulose, polymethacrylates, or other coating agents. Syrups may contain, in addition to the present compounds, sucrose as a sweetening agent and certain preservatives, dyes and colorings and flavors. Materials used in preparing these various compositions should be pharmaceutically pure and non-toxic in the amounts used.

The compounds of Formula I are generally effective over a wide dosage range. For example, dosages per day normally fall within the range of about 0.001 to about 30 mg/kg of body weight. In some instances dosage levels below the lower limit of the aforesaid range may be more than adequate, while in other cases still larger doses may be employed without causing side effects sufficient to require the cessation of therapy, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:

1. A compound of Formula I:

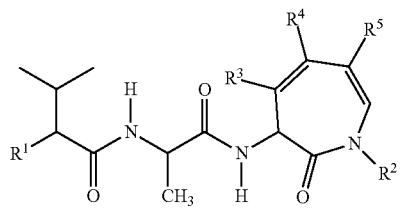

where:
- $R^1$ is hydroxy or fluoro;
- $R^2$ is $C_1$-$C_4$ alkyl;
- $R^3$ is hydrogen or phenyl;
- $R^4$ is hydrogen, phenyl, or $C_1$-$C_4$ alkyl;
- $R^5$ is hydrogen or phenyl; provided that one of $R^3$, $R^4$, and $R^5$ is other than hydrogen and the other two are hydrogen.

2. A compound of claim 1 where $R^4$ is either hydrogen or phenyl.

3. A compound of claim 1 where $R^4$ is phenyl.

4. A compound of claim 3 where $R^1$ is hydroxy and $R^2$ is methyl.

5. The compound:

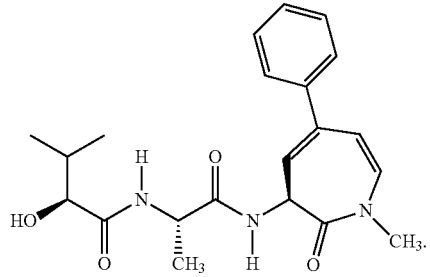

6. A pharmaceutical composition comprising a compound of claim 1 and a pharmaceutically acceptable diluent.

7. A method of treating Alzheimer's disease comprising administering to a patient in need thereof an effective amount of a compound of claim 1.

8. A method of inhibiting the progression of Alzheimer's disease comprising administering to a patient in need thereof an effective amount of a compound of claim 1.

* * * * *

UNITED STATES PATENT AND TRADEMARK OFFICE
CERTIFICATE OF CORRECTION

| | |
|---|---|
| PATENT NO. | : 8,188,069 B2 |
| APPLICATION NO. | : 12/669048 |
| DATED | : May 29, 2012 |
| INVENTOR(S) | : Melinda Joy Hope Miller et al. |

It is certified that error appears in the above-identified patent and that said Letters Patent is hereby corrected as shown below:

Title Page, Col. 2, (Attorney, Agent, or Firm), Line 1, Delete "Nelson" and insert -- Nelsen --, Column 1, Line 7, Delete "60/995,720," and insert -- 60/955,720, --, Column 18, Line 29, In Claim 4, Delete "3" and insert -- 1 --, Signed and Sealed this
Seventeenth Day of July, 2012

David J. Kappos
*Director of the United States Patent and Trademark Office*